United States Patent [19]

Koniger

[11] Patent Number: 5,641,481
[45] Date of Patent: Jun. 24, 1997

[54] COMPOSITION TO CONTROL DERMATOMYCOSES AND THEIR PATHOGENS, PERSPIRATION AND BODY ODOR

[76] Inventor: Helmut Koniger, Maillingerstrabe 8, D-80636 Munich, Germany

[21] Appl. No.: 435,449

[22] Filed: May 5, 1995

Related U.S. Application Data

[63] Continuation of PCT/DE93/01061, Nov. 5, 1993.

[30] Foreign Application Priority Data

Nov. 6, 1992 [DE] Germany ............... 42 37 551.7
Feb. 12, 1993 [DE] Germany ............... 43 04 284.8

[51] Int. Cl.$^6$ ................................ A61K 7/06
[52] U.S. Cl. ............... 424/74; 424/47; 424/65; 424/195.11; 514/844; 514/827; 514/828; 514/845; 514/846; 514/847; 514/848
[58] Field of Search ............... 424/74, 70, 47, 424/195.11, 65; 514/844, 827, 828, 845, 846, 847, 848

[56] References Cited

U.S. PATENT DOCUMENTS 4,933,177  6/1990  Grollier et al. ............... 424/74

*Primary Examiner*—Terressa Mosley
*Attorney, Agent, or Firm*—Dennis H. Lambert

[57] ABSTRACT

The invention concerns a composition containing ingredients of the herb of the equisetum species and ingredients of the herb and/or of the flower of the lavandula species and used in the external prevention and control of dermatomycoses, in particular dermatophytoses, of skin ailments with the clinical appearance of tinea pedis and skin ailments caused by their pathogens at other body locations. The invention further relates to a composition as described above for the treatment and control of bromidrosis, other perspiration and unpleasant body odor, and to control dermatomycosis pathogens and pathogens able to cause the clinical appearance of tinea pedis in textiles, other wear and sanitary articles in contact with the skin, and to deodorize same, and to methods to achieve these effects and a method to prepare the composition of the invention.

12 Claims, No Drawings

COMPOSITION TO CONTROL DERMATOMYCOSES AND THEIR PATHOGENS, PERSPIRATION AND BODY ODOR

This application is a continuation of prior International application number PCT/DE93/01061, filed Nov. 5, 1993, now abandoned, which, in turn, claims priority under 35 USC §119 of prior German national application numbers DE 4237551.7, filed Nov. 6, 1992, and DE 4304284.8, filed Feb. 12, 1993.

1. Field of the Invention

The invention relates to a composition and method for treating and controlling dermatomycoses and their pathogens, perspiration and body odor. In particular, the invention concerns a composition containing herb ingredients of the equisetum species and ingredients of the herb and/or flower of the lavandula species. Furthermore, it relates to the use of said ingredients for external prevention and control of dermatomycoses, in particular dermatophytoses, of skin ailments with clinical appearance of tinea pedis and skin ailments caused by their pathogens at other body locations, and further, bromidrosis, and other perspiration and unpleasant body odor. It also concerns the control by means of such compositions of dermatomycosis pathogens and pathogens that may precipitate the clinical appearance of tinea pedis present in textiles, and other wear and sanitary articles in contact with the skin, and further, the deodorization of same. The invention also relates to a method to achieve said effects and a method to prepare the composition of the invention.

2. Background of the Invention

Dermatomycoses and in particular dermatophytoses are ailments both widely spread and potentially psychologically highly adverse to the patient on account of their frequently cosmetic implications. Tinea pedis ("athlete's foot") in particular may be termed a widespread dermatomycosis considered highly unpleasant. Its occurrence is estimated at 15 to 30% of the population in Europe and North America. It is mainly caused by the ubiquitous dermatophytes, mostly trichophyton rubrum, trichophyton mentagrophytes and epidermophyton floccosum. It may spread to the nails (tinea unguium), to the hands (tinea manus) and to other body parts, and may be introduced together with bacterial infections and/or a fungal infection by means of candida, or a skin ailment, with a clinical appearance practically not different from tinea pedis, which also may extend to other body locations, and may be entirely caused by either or both of the last stated two infections. Differential diagnosis to test for dermatophytes is difficult (dermatophyte cultures require 2–4 weeks at room temperature) and as a rule is not undertaken. Very frequently this ailment is accompanied by bromidrosis (foul smelling perspiration) which is widely considered being caused by bacteria, and consequently raises a serious cosmetic problem.

Predispositional factors in particular for tinea pedis are hyperidrosis (excessive sweating) and acrocyanosis which frequently is accompanied by local hyperidrosis.

When untreated, the ailment is mostly chronic. However, even when treated by the presently available methods (usually long-term treatment) and observance of all required hygienic procedures, it is often hardly curable, and relapse, especially in the presence of the above cited predispositional factors, is frequent (for overview of present-day treatments of dermatomycoses, see O. Braun-Falco et al, Dermatology, Springer, Berlin 1991, pp 219–246, especially the differential diagnosis of tinea pedis on p 228 and its treatments on pp 230–232).

Problems also are encountered when disinfecting wear, especially shoes. As a rule, solutions containing formaldehyde are recommended, which however may trigger allergies and furthermore cannot be considered an ideal resolution on account of the known health dangers of formaldehyde.

Unpleasant body odor arises both from the elimination of foul-smelling substances from the body and from the effects of bacteria and/or oxygen on substances eliminated from the body that initially were without or with little odor but which in the process are converted into strongly odorous decomposition products.

Odor formation can be controlled on one hand by reducing or preventing the separation of the body's elimination products, in particular sweat. Inherently this results in a deodorizing effect. Odor formation may be controlled further by preventing already eliminated separation productions from producing a foul smell, mainly (a) killing the decomposing bacteria, (b) preventing oxygen from effectively reacting (oxidation) by conversion into olfactory components, and (c) chemically or physically binding already formed olfactory components.

Numerous cosmetics are already on the market to control body odor, which, however, all incur some drawbacks. The means which foremost inhibit sweat elimination, for instance astringents based on aluminum salts and especially those based on aluminum hydroxychloride, become effective as a rule only upon extended use, that is, not immediately when perspiration reduction is desired, for instance when there is much bodily or nervous stress. Moreover, the required long-term use permanently constricts the pores even when perspiration inhibition is not required. On the other hand cosmetics with deodorizing effects in the narrow sense affect the volume of perspiration only little or not at all, instead preventing odor formation from already eliminated body separations by destroying the seat decomposing bacteria, that is, they act bactericidally or aseptically.

However means are desirable which shall reduce perspiration where required without acting permanently and which also prevent disagreeable odor formation from already separated body eliminations.

SUMMARY OF THE INVENTION

Accordingly, it is an object of the invention to create a means effectively inhibiting dermatomycoses, in particular dermatophytoses and skin ailments with a clinical appearance resembling tinea pedis which also may arise on other body locations, and further, related bromidrosis and the predispositional factor of hyperidrosis, said means also being effective in disinfecting wear articles and being generally useful as a perspiration inhibiting and deodorizing means.

This problem is solved by the composition defined in claim 1, namely, a composition which contains ingredients of the herbs of plants of the equisetum species and at least one of the herb and the flower of plants of the lavandula species.

The invention furthermore relates to the use of the composition defined in claim 1 as external prophylaxis and control against dermatomycoses, in particular dermatophytoses, skin ailments with the clinical appearance of tinea pedis and the skin disorders generated by their pathogens at other body locations, to control bromidrosis, perspiration and to act as a deodorant, and further, to control the above ailments' pathogens in textiles, in other articles of wear and sanitary use coming in contact with the skin, and to deodorize said articles.

Furthermore, the invention concerns methods to implement the said effects using the composition of the invention, and further, to a method for preparing the composition.

When searching for an effective and rapidly acting means against dermatomycoses, in particular against the widespread ailment with the clinical appearance of tinea pedis and the related skin ailments, and further, against elimination of perspiration and foul body odor, it was surprisingly discovered that a composition containing the ingredients of the green parts of equisetum and the ingredients of the shrub and/or of the flowers of lavandula not only will heal the skin infection within a few days, but furthermore will control in outstanding manner hyperidrosis, foul body odor and bromidrosis, and, most of the time following a single application, will disinfect wear articles, shoes especially included, so effectively that re-infection does not take place, while also deodorizing extremely well said articles.

Equisetum (horsetail), in particular the types equisetum arvense (popularly known as "tin weed", a widespread weed used in earlier times to clean tinware) and equisetum hiemale (Duct rush) are held to have been used in antiquity already as curative herbs. Kneipp recently again raised consideration of equisetum.

In his LEHRBUCH DER BIOLOGISCHEN HEILMITTEL, THIEME, LEIPZIG, 1938, pp 1267–1278, G. Madaus reported on innumerable internal and external folklore applications of different kinds of equisetum, and of significance foremost in the present considerations, on the astringent, styptic effect. Further, he apparently contradictorily reports on a perspiratory effect (manifestly when taken internally, G. Madaus, loc. cit., pp 1273) and control of sweat foot by foot baths and compresses. He also reports their use in controlling fluor albus, ozena, rachitis and gingivitis (G Madaus, loc. cit., pp 1273) by means of equisetum infusions and decoctions.

A more recent popular book on medicinal herbs (Maria Treben, GESUNDHEIT AUS DER APOTHEKE GOTTES, self-published (Verein Freunde der Heilkräuter, no year, but later than 1978) also cites the styptic effect, the effect against sweat feet and the use of equisetum for infections in the mouth and neck (Maria Treben, loc. cit., pp 42–3). Joseph Karl, PHYTOTHERAPIE, Tibor Marczell, 4th ed., 1983, p 133, cites the external application of equisetum arvense for dermatoses, pemphigus, decubitus (bedsores), old wounds and ulcus crurius; Hans Braun, Dietrich Frohne, HEILPFLANZEN-LEXIKON FÜR ÄRTZTE UND APOTHEKER, Fischer, Stuttgart, 1987, p 105, list decoctions, i.e. an extract of equisetum arvense, as an external means against decubitus and rheumatic complaints.

According to H. Braun & D. Frohne, loc. cit. p 1275, the effective ingredients of the equisetum arvense herb are silicic acid (partly in soluble form), flavanoids (quercetin and camphor oil as aglyca), potassium salts and, with a question mark, saponins, whereas J. Karl, loc. cit, and G. Madaus, loc. cit., p 1275, are positive about the presence of saponins.

The use of various kinds of lavandula as medicinal herbs also can be traced at least as far back as the 12th century. Lavandula officinalis Chaix et Vill. (=lavandula angustifolia Mill.; genuine lavender) is foremost among such uses, however other kinds, in particular lavandula spica (=lavandula latifolia Vill.) are cited by diverse authors.

Regarding the herein relevant external application of lavandula discussed in G. Madaus, loc. cit. pp 1723–1725, namely in the form of a bath additive, of the oil, of an extract, of trituration of flowers and/or of a tincture, said author also provides information about antiseptic and pyostatic properties, further about effects on epilepsy and fainting, blood congestion, rheumatism, gout, neuralgia, sciatica, further scabies and fluor albus. Flores lavandulae are said to be calming for migraines and nervous upsets. J. Karl loc. cit. p 203 cites lavender oil as a mild sedative and neuroostimulant, and, with respect to external use, as an odor corrective with calming property and as a hyperaemicum; H. Braun and D. Frohne, loc. cit., p 147, cite lavender oil as a skin irritant in external application.

The earlier literature lists both the flower and the herb as the plant part being used, whereas in recent times only the flowers have been. The main active substances of lavender oil are linalylacetate and further terpenes, also tannins.

Most of the above effects cited for the external application of ingredients of equisetum or lavandula are inherently fairly vague. Most significantly, they rest on usage relayed from times when more precise diagnosis of the particular ailments hardly was possible.

When testing equisetum arvense alone in the form of a diluted extract applied over a number of days, it was found that sweat-foot and perspiration at other body locations was inhibited rather effectively. However, marked and unpleasant skin drying was observed and the skin ailment with the clinical appearance of tinea pedis remained.

Again, lavender alone when deposited over several days in the form of pure lavandulae aetheroleum or diluted with aqueous isopropanol did not improve the clinical appearance of tinea pedis; only temporary odor-correcting and generally skin-pleasing effects could be noted.

It was only the mixture of these two components applied over a number of days which brought about the surprising, synergistic effect in treating this ailment, both as regards the elimination of perspiration in the absence of disagreeable side effects (skin drying) and the elimination of body odor. Bromidrosis was eliminated after a few days and did not recur, and the skin lesions healed completely. Over the treatment span, hyperidrosis was suppressed virtually totally and thereafter also was substantially reduced. Relapses did not occur at all over the observation span (6 months), or could be nipped in the bud by applying the mixture again. Effective shoe disinfection, noticeable by the complete disappearance of the foul smell and the absence of relapses, in most cases could be achieved upon single treatment of said shoes by said mixture, which were left standing for 24 hours.

In the course of the above research, it was found that the above mixture is extremely well suited in general to inhibit hyperidrosis and odors. While equisetum alone is effective in this respect, it entails, however, the unpleasant side effect to markedly dry the skin and to make it rough, whereas lavandula applied alone will be pleasant to the skin but lack any significant inhibition of perspiration. Mixing the two components assures strong and rapidly arising suppression of evaporation, in the absence of skin drying, suppression of the unpleasant body odor, the skin remaining smooth and, furthermore, evincing a highly pleasant and calming effect, presumably on account of the lavender's olfactory component, as reported by the test subjects, such a feature being advantageous especially in stress conditions wherein frequently hyperidrosis conditioned by the autonomous nervous system arises. Using the mixture to inhibit perspiration is also quite advantageous when the commercial sweat-suppressants are precluded on practical grounds (for instance if the hands were to be protected), or if the effect ought to be practically instantaneous, the latter case not being met by the strongest commercial sweat-inhibiting means wherein the active substances are aluminum salts or other inorganic salts with pore-constricting effects.

The biological mechanism of the surprising above-mentioned synergism is not yet clear.

DETAILED DESCRIPTION OF THE PREFERRED EMBODIMENTS

The types equisetum arvense, equisetum hiemale and lavandula officinalis Chaix et Vill. (=lavandula angustofiola Mill.), lavandula spica and lavandula hybrida Rev. are especially preferred as the raw-material plants for the composition of the invention.

The initial substances for a galenic preparation of the mixture of equisetum and lavandula ingredients preferably are an ethanol-aqueous (30:70 vol/vol) extract (1:1 vol/vol) of the former and the pure flower oil of the latter, prepared for instance by steam distillation. However, other raw materials are useful too, for instance dried, triturated herbs, sap pressed out of the herbs, or aqueous equisetum or lavandula infusions, or the triturated flowers or a flower-extract from the latter. Paul Heinz List & Peter C. Schmidt, in TECHNOLOGIE PFLANZLICHER ARZNEIZUBEREITUNG, Wissenschaftliche Verlagsgesellschaft mbH, Stuttgart, 1984, provide an excellent survey of various preparations applicable in this respect.

Where called for, the raw materials may be converted into all galenic forms suitable for external application and all forms for cosmetic and disinfecting applications, for instance powders, salves, creams, gels, lotions, emulsions, solutions, illustratively applied as sprays, and powered sprays (aerosols). Karl Thoma, DERMATIKA, 2nd ed. Munich, 1983 (marketed by Werbe- und Vertriebsgesellschaft DeutscherApothekerm.b.H., Frankfurt, further REMINGTON's PHARMACEUTICAL SCIENCES, 18th ed., Mack Publishing Co., Easton, Pa. 1990, especially pp 1694–1712 (aerosols) offer surveys of pertinent galenicals.

An especially preferred appropriate galenic form also suitable for further uses of the composition of the invention is a solution of an ethanol-aqueous extract composed as above of equisetum and lavandula flower oil in a mixture of ethanol or isopropanol and water, in particular 35% (vol/vol) of isopropanol/water, which is easily applied using an atomizer.

The ratio of the equisetum to lavandula ingredients in the composition of the invention preferably is within the range of 15:100 to 100:15 parts by weight. The concentration of the plant ingredients in the medicinal and cosmetic preparations of the invention foremost depend on the purpose of use (for instance prophylaxis or therapy), on the kind and gravity of the ailment or cosmetic degradation, also on the galenic form. As regards disinfection, concentrations approximately 1 to 40% (vol/vol) are advantageous in the above range of mixture in a vehicle. As regards cosmetics, frequently lesser concentrations than those above suffice to prevent perspiration and unpleasant body odor.

In most instances an advantageous concentration for the therapy of skin ailments evincing the clinical appearance of tinea pedis will be approximately 1.25–10% vol. horsetail extract (1:1 [vol/vol]) in 30% [vol/vol] aqueous ethanol) and an equal amount of undiluted lavender oil. Following thorough washing and drying of the . . . is effectively controlled . . . and also is clearly reduced following its termination.

To disinfect and deodorize the shoes, for example, a solution of the above-described concentration is sprayed into them until they are fully moistened. Following 24 hours after application of such a first spray, typically all unpleasant odor shall have vanished and the shoes may be worn without danger of renewed infection.

When using the composition of the invention in the above-described isopropanol solution as a perspiration and odor inhibiting means, frequently also a lesser concentration than stated above suffices, for instance half that concentration. Even at extreme bodily exertion, perspiration is practically entirely suppressed at least for 30 minutes. As a rule inhibition of perspiration and odor lasts several hours.

Besides vehicles and other pharmacologically inactive ingredients, the composition of the invention may furthermore include accessory substances (inclusive of medicinal, cosmetic and germicidal/inhibiting means). For instance, phthalic acid may be added to cause substantial duration of the lavender oil aroma. Other plant ingredients such as pine-needle oil may be admixed as further odor component or tannin or perfumes.

The invention is elucidated below by means of illustrative embodiments which, however, do not imply restriction on the invention.

EXAMPLE 1

Ingredients of the equisetum-arvense herb were used in the form of an extract (horsetail herb extract, fluid extract 1:1, [vol/vol], extractant 30% [vol/vol] aqueous ethanol, from Dr. Hetterich KG, Fürth).

Ingredients of lavandula officinalis in the form of steam-distilled flower oil with a linanylacetate content of 42.1%-wt (DAB) [Deutsches Arzneibuch] were used (lavender oil [lavandulae aetheroleum] DAB Mont Blanc 38–45%, from Vaselin-Werke Wasserfuhr GmbH, Bonn).

The above ingredients were dissolved in 35% (vol/vol) aqueous isopropanol with agitation in an atomizer flask. In some cases the solution was slightly cloudy, indicating that part of the raw materials were present in emulsion. However the emulsion did not de-mix even after extended storage.

Preparations of the following concentrations of the above raw materials in 35% (vol/vol) aqueous isopropanol were made:

| Preparation Nr. | Horsetail Extract (1:1) | Lavender oil |
| --- | --- | --- |
| 1 | 10% (vol/vol) | 10% (vol/vol) |
| 2 | 3% (vol/vol) | 3% (vol/vol) |
| 3 | 7% (vol/vol) | 3% (vol/vol) |
| 4 (control) | 20% (vol/vol) | — |
| 5 (control) | — | 20% (vol/vol) |
| 6 (control) | 7% (vol/vol) | — |
| 7 (control) | — | 7% (vol/vol) |

Furthermore, 0.8% (weight/volume) of phthalic acid was added to the samples 1,2,3,5 and 7 to extend the olfactory effect of lavender oil.

EXAMPLE 2

The preparation Nr. 1 of Example 1 was sprayed on the affected foot parts of four test subjects evincing marked appearance of tinea pedis already spread through the gaps between the toes and who had been previously unsuccessfully treated with conventional medicines (differential diagnosis was absent from all cases), said spraying being carried out mornings, noon and evenings following thorough washing and drying of the feet's affected areas until latter were totally covered with a film of the preparation. Following volatilization of the solvents, socks/stockings and shoes were worn.

Bromidrosis and itching/burning completely disappeared following 3, 4 (two test subjects) or 7 days. Sweat foot was practically suppressed during the treatment time interval and even after termination of treatment all test subjects reported substantial decrease in perspiration. During the time of observation (6 months), one relapse took place (presumably because of swimming-pool infection), said relapse however being nipped in the bud by repeating the above treatment for 3 days.

EXAMPLE 3

All shoes of the test subjects in Example 2 were sprayed with the composition Nr. 1 of the invention till well moist and were left to stand 24 hours.

Only in one instance did the typical tinea pedis odor linger, and the treatment was repeated. Following healing of tinea pedis, the shoes were worn again and except for the one cited case, which however is unlikely being due to the shoes, no re-infection took place.

CONTROL TEST 1

Prior to the treatment with the composition Nr. 1 of the invention of Example 1, two of the test subjects of Example 2 were treated with the preparation Nr. 4 (control preparation) for 7 days in the same manner as in Example 2. Perspiration was suppressed similarly to Example 2. However, the suppression was

EXAMPLE 5

Three male test subjects washed their axillas in the morning for four days with commonplace, unscented soap and thereupon sprayed the preparation Nr. 2 of Example 1 into the left axilla, the right one remaining untreated. All three test subjects then carried out their usual (fairly physical) work. Six hours later the odor of the particular left and right axillas was compared. It was found that the left axillas treated in the manner of the invention smelled significantly less of sweat than the untreated right axillas. The subjects agreed that the deodorant was very gentle to the skin.

EXAMPLE 6

The shoes of two persons giving off sweat-foot odor were sprayed till moist with the preparation Nr. 3 of Example 1 and left to stand 24 hours. In both cases the sweat-foot odor disappeared completely.

Although the invention has been illustrated and described in detail herein, it is to be understood that various changes and modifications may be made therein without departing from the spirit and scope of the invention as defined in the appended claims.

What is claimed is:

1. A composition which contains ingredients of the herbs of plants of the equisetum species and at least one of the herb and the flower of plants of the lavandula species.

2. A composition as defined in claim 1, wherein the ingredients of plants of the equisetum species are obtained by extraction and the ingredients of the lavandula species are a flower oil.

3. A composition as defined in claim 1, wherein the extract is obtained by extracting with 30% (vol/vol) aqueous alcohol.

4. A composition as defined in claim 1, wherein the plants of the equisetum species are selected from the group consisting of equisetum arvense and equisetum hiemale, and the plants of the lavandula species are plants selected from the group consisting of lavandula officinalis Chaix et Vill. (=lavandula angustifolia Mill.; genuine lavender), lavandula spica (=lavandula latifolia Vill.) and lavandula hybrida Rev.

5. A composition as defined in claim 1, wherein the equisetum ingredients are present in ratios of 15:100 to 100:15 parts (weight/weight) to the lavandula ingredients.

6. A composition as defined in claim 1, wherein the composition contains at least one vehicle.

7. A composition as defined in claim 6, wherein the vehicle is acceptable for either or both pharmacological and cosmetic external application.

8. A method for external prevention and control of dermatomycoses, in particular dermatophytoses, skin ailments with the clinical appearance of tinea pedis and skin ailments caused by the pathogens of said first mentioned skin ailments at other body locations, wherein a composition which contains ingredients of the herbs of plants of the equisetum species and of at least one of the herb and the flower of plants of the lavandula species is applied on an affected body location.

9. A method for treating bromidrosis, perspiration and body odor, wherein a composition which contains ingredients of the herbs of plants of the equisetum species and of at least one of the herb and the flower of plants of the lavandula species is applied to an affected body location.

10. A method to control dermatomycosis pathogens and pathogens of skin ailments which are able to cause the clinical appearance of tinea pedis, in textiles, and other wear and sanitary articles in contact with the body, wherein said textiles, other wear and sanitary articles are treated with a composition which contains ingredients of the herbs of plants of the equisetum species and of at least one of the herb and the flower of plants of the lavandula species.

11. A method for controlling odors in textiles, and other wear and sanitary articles in contact with the body, comprising treating said textiles, other wear and sanitary articles with a composition which contains ingredients of the herbs of plants of the equisetum species and of at least one of the herb and the flower of plants of the lavandula species.

12. A method for preparing a composition which contains ingredients of the herbs of plants of the equisetum species and of at least one of the herb and the flower of plants of the lavandula species, comprising appropriately mixing the ingredients.

* * * * *

UNITED STATES PATENT AND TRADEMARK OFFICE
CERTIFICATE OF CORRECTION

PATENT NO. : 5,641,481

DATED : June 24, 1997

INVENTOR(S) : Helmut Königer

It is certified that error appears in the above-identified patent and that said Letters Patent is hereby corrected as shown below:

Column 7, line 27, insert the following after "was":

--accompanied by a marked feeling of dryness, and the odor of tinea pedis as well as itching and burning would not entirely disappear. Following treatment, the tinea pedis symptoms came back in full.

CONTROL TEST 2

Prior to treatment with the preparation Nr. 1 of Example 1, two further test subjects were treated with the preparation Nr. 5 (control preparation) for 7 days in the same manner as in Example 2. Significant reduction in perspiration did not take place, and itching and burning, even though reduced, still were present, and the lavender aroma merely overcame the tinea pedis odor. The tinea pedis symptoms returned in full force after the treatment was completed.

EXAMPLE 4

(A) the preparation of the invention Nr. 3 of Example 1 was sprayed on the hands of two tennis players after 30 minutes of play, who had been hampered by extreme hand perspiration during playing, until the spray left a film on their hands. The film was allowed to dry for a few minutes. After about 4 to 6 minutes, no perspiration was observable. The two players' hands remained practically dry for a time interval of at least 30 minutes.

This procedure was repeated with the control preparations Nrs. 6 and 7. The control preparation Nr. 6 did in fact prevent perspiration over

UNITED STATES PATENT AND TRADEMARK OFFICE
CERTIFICATE OF CORRECTION

PATENT NO. : 5,641,481
DATED : June 24, 1997
INVENTOR(S) : Helmut Königer

Page 2 of 3

It is certified that error appears in the above-identified patent and that said Letters Patent is hereby corrected as shown below:

the cited time interval, but both players complained of strong dryness of the hands which was unpleasant when holding the rackets. While the control solution Nr. 7 was found pleasant to the skin, it failed to significantly inhibit perspiration.

(B) Three female test subjects, suffering from hand hyperidrosis-induced conditioned by the autonomous nervous system interfering with their professions, sprayed as needed either the preparation of the invention Nr. 2 or the control preparations Nrs. 6 and 7, not knowing the ingredients of said sprays, on their hands. They reported in unison that the preparation of the invention Nr. 2 offered the best combination of perspiration inhibition and feeling of softness, whereas the control preparation Nr. 6 was felt to be desiccant and the control preparation Nr. 7 to be inadequately sweat-inhibiting.--

UNITED STATES PATENT AND TRADEMARK OFFICE
CERTIFICATE OF CORRECTION

PATENT NO. : 5,641,481
DATED : June 24, 1997
INVENTOR(S) : Helmut Koniger

It is certified that error appears in the above-identified patent and that said Letters Patent is hereby corrected as shown below:

Column 5, lines 62 and 63, change to read as follows:

--ough washing and drying of the feet, such a solution is sprayed twice to three times daily on the affected locations until these locations are coated with a film of the solution which then is allowed to dry before wear is put on. Following several days, as a rule three to seven days, the complaints accompanying tinea pedis and bromidrosis will have disappeared completely, and hyperidrosis is effectively controlled during the duration of the treatment and also is clearly reduced following its termination.--

Change the spelling of the inventor's name from "Helmut Koniger" to --Helmut Königer--.

Signed and Sealed this

Thirty-first Day of March, 1998

Attest:

Attesting Officer

BRUCE LEHMAN

Commissioner of Patents and Trademarks